United States Patent [19]

Smith et al.

[11] 4,021,302

[45] May 3, 1977

[54] CELL CULTURES

[75] Inventors: Sidney Edwin Smith; Kevin Joseph O'Reilly; John Prydie, all of London, England

[73] Assignee: Burroughs Wellcome & Co., Inc., Tuckahoe, N.Y.

[22] Filed: Aug. 20, 1975

[21] Appl. No.: 606,025

Related U.S. Application Data

[60] Continuation of Ser. No. 318,234, Dec. 26, 1972, abandoned, which is a continuation of Ser. No. 31,802, April 24, 1970, abandoned, which is a division of Ser. No. 615,922, Feb. 14, 1967, Pat. No. 3,520,972.

[30] Foreign Application Priority Data

Feb. 18, 1966   United Kingdom ............... 7258/66
Sept. 8, 1966   United Kingdom ............. 40225/66

[52] U.S. Cl. ................................................ 195/1.8
[51] Int. Cl.² ......................................... C12K 9/00
[58] Field of Search .......................... 195/1.3, 1.8

[56] References Cited

UNITED STATES PATENTS

| | | | |
|---|---|---|---|
| 3,255,080 | 6/1966 | Emery ................................ | 195/1.3 |
| 3,264,187 | 8/1966 | Slater ................................. | 195/1.3 |
| 3,293,130 | 12/1966 | Slater et al. ........................ | 195/1.3 |

*Primary Examiner*—Sam Rosen
*Attorney, Agent, or Firm*—DeLio and Montgomery

[57] ABSTRACT

Cell culture comprising a novel cell strain in suitable nutrient medium, wherein the novel cell strain is produced by disaggregated feline embryo tissue cell and serially passaging the same from about the 20th to about the 48th passage level, so as to be cultured and subcultured with the resultant cell strains remaining substantially diploid, typically fibroblastic and substantially free from morphological transformations. Subculturing is facilitated by treatment of a confluent sheet of the disaggregated cells chelating agent before each transfer into a new batch of nutrient medium.

1 Claim, No Drawings

CELL CULTURES

This is a continuation of application Ser. No. 318,234, filed Dec. 26, 1972, now abandoned. Ser. No. 318,234 is a continuation of Ser. No. 31,802, filed Apr. 24, 1970, now abandoned. Ser. No. 31,802 is a division of Ser. No. 615,922, filed Feb. 14, 1967, now U.S. Pat. No. 3,520,972.

This invention relates to cell strains, particularly to a novel type which is derived from feline embryo cells, to the growth of viruses thereon, and is vaccines containing such viruses.

It has been known to grow the feline infectious enteritis (panleucopoenia) virus on a primary tissue culture prepared by trypsinizing infected cat kidney cells. This method, has however suffered from the disadvantage that the possibility of contamination with other, not easily detectable viruses could not be excluded, whilst the available quantity of such a tissue culture is limited at certain times of the year, and represents a heterogenous population of cells, which hinders the production of the virus for the purposes of experimentation or preparation of vaccines. Furthermore, modification and attenuation of the feline infectous enteritis virus to primary kitten kidney culture is impracticable because of the danger of contamination with virulent feline infectious enteritis virus which may at times be present in the primary kitten tissue cultures used.

It has generally been recognized that the lack of suitable contamination free host cells or cell strains capable of supporting pathogen viruses of interest greatly hindered research and development efforts to provide viruses suitable for use in vaccines to combat animal and human diseases.

A new cell strain comprising cells which are derived from the feline embryo lung and has now been found to be capable of supporting pathogenic viruses, particularly the feline infectious enteritis virus, feline rhinotracheitis virus and deline picornaviruses. It has also been found that cell strains derived from feline ambryo kidney or heart, or the mixture thereof, or from embryo skin, muscle, amnion (placenta), tongue, liver or gut, or the whole embryo or embryo carcase, are likewise suitable for supporting pathogenic viruses. Furthermore, it has become possible to attenuate for instance the feline infectious enteritis virus by means of passaging the virus in cultures of such feline embryonic cell strains.

According to the present invention in the first aspect there is provided a cell strain, comprising cells which are derived from feline embryos and are capable of supporting pathogenic viruses. In a second aspect there is provided a method for producing a cell strain as hereinbefore defined, in which the appropriate feline embryo tissue is disaggregated and then cultured or subcultured by serial passages in a nutrient medium.

In a third aspect there is provided a method for growing a virus, wherein a culture of the cell strain, as hereinbefore defined, is infected with a virus to which the strain is subceptible, and the strain is then cultured in a nutrient medium. In a fourth aspect there is provided an antigenic material, which is obtained from a virus grown on that cell strain, and a vaccine presenting the antigenic material in an administrable form and dosage.

In a particular aspect an attenuated strain of the feline infectious enteritis virus is provided by a method which comprises passaging a virulent strain of the virus in cultures of feline embryonic cell strains, as hereinbefore defined, until the virus loses its infectivity, but still retains its immunogenicity. The strains so obtained can be presented in the form of a vaccine for the immunisation of cats against feline infectous enteritis.

It is well-known that cell strains are cell systems which are derived from cells removed from living organisms and are capable of being cultured in vitro in a nutrient medium while remaining substantially diploid with the chromosomal composition unchanged. For the purposes of the present invention any medium known in the art, which provides the necessary physical and chemical conditions and nutritional composition for culturing or subculturing, i.e. the maintenance, individual growth and multiplication of these cells, may be used. It has, however, been preferred to use Eagle's Basal Medium with some bovine serum, and particularly the same medium with tryptose phosphate broth and with twice the usual amount of amino acids and vitamins. The pH of the medium is kept between pH 6.8 and 7.8 for instance by the use of a buffering agent.

Cell strains according to the present invention provide host cells for growing viruses. These cells are free from viral contamination and represent a substantially constant degree of viral susceptibility. They can be made available in practically any quantity independently of the seasonal fluctuations experienced with primary tissue cultures directly obtained from young kittens.

The cat embryo used for the purposes of the present invention may preferably be of the size from about 1 cm, to 4.5 cm. The embryo or part of it is removed under aseptic conditions and disaggregated mechanically or with a suitable enzyme preparation in a buffered saline solution. The resulting cell suspension is then transferred into the containers holding the nutrient medium and is cultured within the temperature range of 32° C to 39° C., preferably within 35° C to 37.5° C. To facilitate subculturing it is customary to treat the confluent sheets of the cells of the strain with trypsin and an innocuous chelating agent before each transfer into new medium.

The lung tissue may conveniently be removed from a cat embryo at about 5 to 7 weeks gestation under sterile conditions and disaggregated mechanically or with a suitable enzyme preparation in a buffered saline solution. The resulting cell suspension is then transferred into the containers holding the nutrient medium and is cultured within the temperature range of 32° C to 39° C, preferably within 35° C to 37.5° C. To facilitate subculturing it is customary to treat the confluent sheets of the cells of the strain with trypsin and an innocuous chelating agent before each transfer into new medium.

It has been observed that the cells of the strain multiply at a rate which represents a doubling of their number every 2 to 3 days. The cell strain according to the present invention is capable of supporting a number of viruses to which they are susceptible in this respect. Examples for such virus are the feline infectious enteritis virus, feline rhinotracheitis virus, feline picornaviruses and the bovine herpes virus. The picornaviruses include those feline viruses which have properties resembling enteroviruses, rhinoviruses, and also other viruses with properties intermediate between enteroviruses and rhinoviruses.

In order to infect the cell strain with the virus, the strain may be mixed with a saline suspension of the virus, for instance obtained from the exudate of an infected animal or from other sources. In the case of the feline infectious enteritis virus, it has been preferred to use feline infectious enteritis infected spleen or small intestine of cats, and innoculate the same into cultures of the feline embryonic cell strain.

The virus usually produces recognisable changes or cellular degeneration in the strain. When the virus is present in a sufficient quantity, the culture is tested for immunogenic potency and toxicity. If necessary, the virus is attenuated or further attenuated by serial passages in the cell strains provided by the present invention, or is inactivated by the use of suitable chemical or physical agents. The antigenic material to obtained is either used to produce antibodies for passive immunisation or is used as a vaccine by administering the same into warm blooded susceptible animals.

The following Examples illustrate the invention.

EXAMPLE 1

Lung tissue was removed from 2 cat embryos at about 6 weeks gestation. The tissue was disaggregated with a 0.25% solution of trypsin (Nutritional Biochemicals Co. 1/300) in a phosphate buffered saline solution described by Dulbecco et al., *J. exp. Med.*, 1954, 99, 167. The resulting suspension was needed at $5 \times 10^6$ cells to a 4 oz. (112 ml.)- medical flat bottle, which contained Eagle's Basel Medium (80 parts by volume) (of. Eagle H., *Science*, 1955, 122, 504), modified to have twice the usual amount of amino acids and vitamins, tryptose phosphate broth (10 parts by volume) and bovine serum (10 parts by volume) as a sterile solution.

The monolayer cultures so formed were subcultured by serially passaging the content of one flask into 2 or 3 flasks on average twice weekly. The cells were resuspended for this purpose with a 0.05% solution of sodium edetate in a 0.1% solution of trypsin in the above type of phosphate buffered saline.

It was observed that the cells were typical fibroblasts and remained substantially diploid up to the 40th passage. No morphological transformation occurred up to the 100th passage, although chromosome abnormalities became increasingly common.

Stocks of cells up to the 20th passage level were maintained at $-190°$ C in a growth medium with 10 dimethyl sulphoxide added.

In another, similar experiment a medium containing Eagle's Basal Medium (90 parts by volume) and bovine serum (10 parts by volume) was used, but the cells did not grow so rapidly.

EXAMPLE 2

Embryos (also about 2.5 cm.) were removed from pregnant cats and were chopped into fine fragments. The tissue was disaggregated with a 0.25% solution of trypsin (Nutritional Biochemicals Co. 1/300) in a phosphate buffered saline solution. The resulting suspension was seeded at $5 \times 10^6$ cells to a 4 oz. (112 ml.)-medical flat bottle, which contained Eagle's Basal Medium (80 parts by volume) modified to have twice the usual amount of amino acids and vitamins, tryptose phosphate broth (10 parts by volume) and bovine serum (10 parts by volume) as a sterile solution.

The monolayer cultures so formed were subcultured by serially passaging the content of one flask into 2 or 3 flasks, on average twice weekly, later once a week. The cells were resuspended for this purpose with a 0.05% solution of sodium edetate in a 0.1% solution of trypsin in the above type of phosphate buffered saline.

It was observed that the cells were typical fibroblasts and remained substantially diploid up to the 48th passage.

Stocks of cells up to the 20th passage level were maintained at $-190°$ C in a growth medium with 10% dimethyl sulphoxide added.

Similar experiments were carried out with cat embryos carcase varying in size from about 1 cm. to 4.5 cm., with embryo carcase and with the following parts of the cat embryo; kidney, heart, heart and lung mixture, skin, muscle, gut, amnion (placenta), tongue and liver. Satisfactory cell strains were obtained from all these tissues.

EXAMPLE 3

Confluent sheets of the cell strain were obtained and treated with sodium edetate, as described in Example 1 or 2, and the cells dispensed into test tubes (150 × 50 cm.) containing cover slips (no. 1. 22 × 10). To each test tube, about $2.0 \times 10^5$ cells in 2 ml. medium were added, and the tubes were incubated at 37° C while inclined at an angle of about 10°.

A confluent sheet of cells was formed on cover slips 24 to 48 hours after seeding. The medium contained 77.5 of Eagle's Basal Medium modified as defined in Example 1, bovine serum (10%), tryptose phosphate broth (10%) and a 4.4% sodium hydrogen carbonate solution (2.5).

An appropriate dilution (0.25 ml.) of the feline infectious enteritis virus was added to the cells present in the above media. The test tubes were incubated at an angle of about 10° at a temperature of 37° C.

The virus produced recognisable changes in the nucleus when the cells were stained with haematoxylin and eosin. At about 18 hours after infection, the infected nuclei (about 1-2% of all the nuclei) took up more haematoxylin than the non-infected nuclei. This was followed in the next 6 hours by enlargement of the nucleoli, homogenous darkening of the other nuclear contents and the development of a clear zone surrounding the nucleolus or nucleoli, if more than one present, and another clear zone immediately inside the nuclear membrane. During the next 24 hours the infected cells appeared to shrink and stain almost black before finally detaching from the coverslip. About 5 to 10% of all nuclei showed the above changes during the first two days following infection.

Similar experiments were carried out with all the other cell strains obtained according to the last paragraph of Example 1. The virus grew satisfactorily on all these new strains.

EXAMPLE 4

Confluent sheets of cells obtained from whole embryos were prepared in test tubes as described in Example 2. A sample of nasal or ocular exudate of a cat suffering from feline rhinotracheitis was mixed with the phosphate-buffered saline solution (2.0 ml.), referred to in Example 1, containing also 200 units of penicillin and 100 mg. of streptomycin per milliliter.

The nutrient medium was removed from the cell strain monolayer in five separate tubes, replaced with the exudate-buffer mixture and incubated at 37° C for 2 hours. The exudate buffer mixture was then removed and the cells washed with fresh sterile buffer solution. The infected tubes containing fresh nutrient medium (1.5 ml. per tube) were then incubated at 37° C in fresh nutrient medium (1.5 ml.).

Daily microscopic examination of the infected cultures and control cultures, prepared with sterile saline solution instead of the exudate-buffer mixture, followed.

During the next few days the microscopic appearance of the cells in the control tubes remained normal. In the infected tubes, areas of abnormal cells appeared within 48 hours. These areas were discretely scattered throughout the cell sheet and consisted of rounded cells showing increased refractility. The area of affected cells were clearly demarcated from the surrounding cells of normal appearance in the early stages. As infection progressed the areas of abnormal cells became larger and more numerous until the entire cell sheet was involved by the 4th to 6th day. In the later stages of infection, some cells detached from the glass leaving clear spaces in the cell sheet. To the naked-eye, the cell sheet took on a "cloudy" appearance. Various tests applied to the fluid and/or cells from infected tubes demonstrated that the agent responsible for these cellular changes was a virus, and still further tests established the identity of the virus as feline rhinotracheitis virus. Other tests demonstrated that the infected cultures were free of other micro-organisms. The virus could be transmitted serially to fresh tube cultures of the same cell strain in which similar cellular degenerative changes took place. Suitable dilution experiments further demonstrated that multiplication of the virus had taken place.

EXAMPLE 5

A further experiment was carried out according to the method described in Example 3 but using a cell strain obtained from the embryonic lung. It was found that this virus also grows well on such cell strains, and results similar to those described in Example 4 were attained.

EXAMPLE 6

Confluent sheets of the cell strain were obtained in test tubes as described in Example 1. A sample of nasal or ocular exudate of a cat suffering from "feline influenza", providing thereby a source of feline picornavirus, was mixed with the phosphate-buffered saline solution (2.0 ml.), referred to in Example 1, containing also 200 units of penicillin and 100 μg. of streptomycin per milliliter.

The nutrient medium was removed from the cell strain monolayer, and was replaced with the exudate-buffer mixture and incubated at 37° C for 2 hours. The exudate buffer mixture was then removed and the cells washed with fresh sterile buffer solution. The infected cell strain was then incubated at 37° C in a fresh nutrient medium (1.5 ml.).

Daily microscopic examination of the infected culture and a control culture, prepared with sterile saline solution instead of the exudate-buffer mixture, followed. It was found that the cellular degeneration (cythopatic effect) which appeared after 2 to 7 days of incubation, was not unlike that produced by human picornaviruses, for example the poliomyelitis virus. The virus could be transferred by serial passages in cultures of the cell strain, and suitable dilution experiments demonstrated that multiplication of the virus in the cell strain had taken place. Further tests demonstrated that the cultures so obtained by serial passages were free of contaminating other microorganisms.

EXAMPLE 7

The virus of feline infectious enteritis was recovered from both the spleen and small intestine taken from infected cats at the height of the disease, and inoculated into cultures of a feline embryonic lung cell strain. To test for intranuclear changes, the cultures were stained with haematoxylin and eosin. When changes were clearly evident — 3 to 5 days after infection of the cultures — the infected cultures were stored frozen at −30° C.

The virus stored frozen at −30° C was later thawed and passaged in non-infected cultures of feline embryonic cell strains. At the appropriate time, as judged by the presence of intranuclear changes, the infected cultures of cell strains were again stored frozen at −30° C until the next passage.

When passing the virus in feline embryonic cell strains, it was customary to add the virus simultaneously with the cells and growth media to the culture vessel. The culture of embryonic cell strains containing the virus inoculum was incubated at 37° C.

The virus strain, for which attenuation for cats is claimed, was serially passaged as described above eight times in feline embryonic lung cell strains and then five times in strains obtained from the whole feline embryo. An aliquot was passaged twice more in strains obtained from the whole feline embryo. Another sample, however, was passaged once in a feline whole-embryo cell strain followed by two or three passages in feline embryonic lung cell strains.

The eighth passage of the attenuated strain of feline infectious enteritis virus was tested for innocuity in two 4-month old kittens. Each kitten was injected subcutaneously with 1.0 ml. of virus infected tissue culture fluid and cells, which was equivalent to 200 tissue culture infective doses. Neither kitten showed any clinical illness although the total count of circulating leucocytes was depressed from the third to the ninth days. Rectal swabs were obtained daily from the kittens from the second to the ninth days after inoculation. Tissue cultures inoculated with these swabs did not show any evidence of virus.

On the twenty-first day these two kittens, together with two uninoculated control kittens of similar age, were challenged orally with 1.0 ml. of a 10% suspension of liver and spleen in 10% horse serum broth. The liver and spleen were obtained from a typical fatal case of feline infectious enteritis. The inoculated cats remained clinically normal throughout the challenge period. The uninoculated control cats, however, becomes pyrexic on the fifth day after challenge, lost body condition, were dull and were significantly leucopoenic,

| | Geometric mean leucocyte counts ($\times 10^3$) | | | | | | | | | |
|---|---|---|---|---|---|---|---|---|---|---|
| Days | 1 | 2 | 3 | 4 | 5 | 6 | 7 | 8 | 9 | 10 |
| After inoculation | 8.8 | 11.2 | 9.7 | 6.8 | 4.5 | 6.0 | 6.8 | 5.8 | 6.7 | 10.1 |

| | Geometric mean leucocyte counts (×10³) | | | | | | | | | |
|---|---|---|---|---|---|---|---|---|---|---|
| Days | 1 | 2 | 3 | 4 | 5 | 6 | 7 | 8 | 9 | 10 |
| After challenge | | | | | | | | | | |
| inoculated kittens | 19.3 | 10.1 | 10.7 | 9.3 | 8.2 | 8.4 | 12.3 | 8.4 | 12.1 | — |
| uninoculated kittens | 10.6 | 11.7 | 4.9 | 6.6 | 4.6 | 3.8 | 4.3 | 5.3 | 6.5 | — |

The kittens were bled before inoculation and before and after challenge and the serum examined for neutralizing antibody.

| | Serum neutralizing antibody | | |
|---|---|---|---|
| Kitten number | Pre-inoculation | Pre-challenge | Post-challenge |
| Inoculated | | | |
| 233 | <2* | 640 | 640 |
| 234 | <2 | 640 | 2560 |
| Uninoculated | | | |
| 235 | NT** | 2 | 640 |
| 236 | NT | 2 | 640 |

*Reciprocal of serum dilution
**Not tested

The 15th passage of this attenuated strain of feline infectious enteritis virus was tested in kittens for innocuity and antigenicity, and for infectivity for uninoculated in-contact kittens. Virus was grown in the feline embryo cell strain and kittens were inoculated subcutaneously with 1.0 ml. of vaccine. The experiment was carried out in two parts, A and B.

A. First, one 4-month old kitten was vaccinated with $1.6 \times 10^3$ tissue culture infective doses of virus. The kitten remained healthy and there was no evidence of leucopoenia or pyrexia and no virus was recovered from the faeces during the first 15 days of the experiment. Two 4-month old kittens and four 3-month old kittens were kept in contact with the vaccinated kittens. None of these kittens showed any sign of ill health, leucopoenia or pyrexia.

B. In the second part of the experiment, six 6–7-month old cats were vaccinated with $1.6 \times 10^3$ tissue culture infective doses of virus. These cats also remained healthy.

The animals used in the above experiments were bled immediately before vaccination and three weeks later. The sera were examined for neutralising antibody.

| | Serum neutralizing antibody | |
|---|---|---|
| Cat number | Pre-vaccination | Three weeks post-vaccination |
| A. Inoculated | | |
| 238 | <10 | 1,000 |
| Non-inoculated | | |
| In contact | | |
| 237 | <10 | <5 |
| 239 | <10 | <5 |
| 240 | <10 | <5 |
| 241 | <10 | <5 |
| 243 | <10 | <5 |
| 244 | <10 | <5 |
| B. Inoculated | | |
| 223 | <5 | 100 |
| 224 | <5 | 1,000 |
| 225 | <5 | 1,000 |
| 226 | <5 | 1,000 |
| 228 | <5 | 1,000 |
| 229 | <5 | 1,000 |
| 230 | <5 | 10,000 |

In another experiment three kittens aged three months were vaccinated subcutaneously with 1.0 ml. of virus at the eighteenth passage level and propagated in a feline embryonic lung cell strain. This amount of virus is equivalent to $1.6 \times 10^5$ tissue culture infective doses. These kittens, together with two uninoculated in-contact kittens of the same age, remained healthy and showed no evidence of leucopoenia or pyrexia.

Serum samples were obtained from the vaccinated kittens immediately before inoculation and 11 and 22 days later. The uninoculated in-contact kittens were bled at the same time. All the sera were examined for neutralising antibody.

| | | Post-vaccination (days) | |
|---|---|---|---|
| | Pre-vaccination | 11 | 23 |
| Vaccinated Kittens | | | |
| 247 | <10 | 100 | >10,000 |
| 250 | <10 | 10,000 | >10,000 |
| 252 | <10 | >10,000 | >10,000 |
| Uninoculated In-contact Kittens | | | |
| 251 | <10 | 10 | <10 |
| 254 | <10 | 10 | <10 |

It has been concluded that this strain of feline infectious enteritis (panleucopoenia) virus, grown and passaged in feline embryonic cell strains, is antigenic, stimulates in cats the production of homologous neutralising antibodies, and is not spread from vaccinated kittens to in-contact susceptible kittens.

EXAMPLE 8

Roux bottles, each containing 12 to $15 \times 10^6$ cells in 100 ml. growth media, as described in Example 7, were incubated at 37° C for 24 hours. The confluent cell sheets were washed once with phosphate buffered saline solution pre-warmed to 37° C, and were inoculated with 10 ml. of an undiluted feline infectious enteritis virus suspension, which was obtained from the 15 to 18th tissue culture passage stage described in Example 7 and represented $1.6 \times 10^6$ tissue culture infective doses (TCID) of the virus.

10 ml. of the medium S.M. 199 (cf. Morgan et al., Proc. Soc. Exp. Biol. Med., 1950, 73, at p. 6), containing also 0.5 ml. of a 4.5% solution of sodium hydrogen carbonate with the usual amounts of penicillin and streptomycin, was added to the culture, and the mixture was incubated at 37° C for 72 hours.

The culture was then rapidly frozen and thawed three times, and was used and tested as described in Example 7. Satisfactory results were obtained.

When necessary, the freeze-thawed preparation was again freezed, and stored at −65° C.

What we claim is:

1. A cell culture comprising a cell strain and a suitable nutrient medium therefor, wherein said cell strain is a feline embryo cell strain produced by disaggregating by chemical or mechanical means feline embryo tissue cells susceptible to feline infectious enteritis virus and serially passaging said cells up to at least the 20th passage level and at most the 48th passage level in a suitable nutrient media, said nutrient medium having a pH between 6.8–7.8 and a temperature in the range of 32° C to 39° C, so as to be cultured and sub-cultured, wherein said sub-culturing is facilitated by treating the confluent sheet of said cells with a chelating agent before each transfer into a new batch of suitable nutrient medium, said resultant cell strains remaining substantially diploid, typically fibroblastic, and substantially free from morphological transformations.

* * * * *

UNITED STATES PATENT OFFICE
CERTIFICATE OF CORRECTION

Patent No. 4,021,302  Dated May 3, 1977

Inventor(s) Sidney Edwin Smith et al

It is certified that error appears in the above-identified patent and that said Letters Patent are hereby corrected as shown below:

Column 1, line 40, "deline" should be --feline--; line 41, "ambryo" should be --embryo--; line 61, "subceptible" should be --susceptible--. Column 3, line 26, "needed" should be --seeded--; line 46, after "10" insert --%--. Column 4, line 10, delete "carcase"; line 21, "cm" should be --mm--; line 27, after "77.5" insert --%--; line 30, after "2.5" insert --%--. Column 5, line 12, "area" should be --areas--. Column 6, line 26, "passing" should be --passaging--; line 60, "comes" should be --came--; bottom of page, in line entitled "After inoculation", under "Days 7", change "6.8" to --6.1--. Column 7, line 34, "$10^3$" should be --$10^5$--. Column 8, line 26, under "Post-vaccination (days)", "23" should be --22--.

Signed and Sealed this

Sixth Day of September 1977

[SEAL]

Attest:

RUTH C. MASON  
Attesting Officer

LUTRELLE F. PARKER  
Acting Commissioner of Patents and Trademarks